| United States Patent [19] | [11] | 4,450,301 |
|---|---|---|
| McMillan et al. | [45] | May 22, 1984 |

[54] PROCESS FOR CONVERTING METHANOL TO FORMALDEHYDE

[75] Inventors: William P. McMillan; Charles C. Hobbs, Jr.; H. Robert Gerberich, all of Corpus Christi, Tex.; Michael L. Junker, Lake Charles, La.

[73] Assignee: Celanese Corporation, New York, N.Y.

[21] Appl. No.: 435,848

[22] Filed: Oct. 21, 1982

[51] Int. Cl.³ ............................................. C07C 47/052
[52] U.S. Cl. .................................... 568/473; 568/471; 568/472
[58] Field of Search .......................... 568/473, 471, 472

[56] References Cited

U.S. PATENT DOCUMENTS

| 1,937,381 | 12/1931 | Bond | 568/473 |
|---|---|---|---|
| 1,968,552 | 7/1934 | Bond | 568/473 |
| 2,462,413 | 2/1949 | Meath | 568/473 |
| 2,908,717 | 10/1959 | Eguchi et al. | 568/473 |
| 3,174,911 | 3/1965 | Webb et al. | 568/473 |
| 3,415,886 | 12/1968 | McClellan | 568/473 |
| 3,959,383 | 5/1976 | Northeimer | 568/473 |
| 4,076,754 | 2/1978 | Kiser et al. | 568/473 |
| 4,097,535 | 6/1978 | Yang et al. | 568/473 |
| 4,119,673 | 10/1978 | Aicher et al. | 568/473 |
| 4,343,954 | 8/1982 | Hoene | 568/473 |
| 4,358,623 | 11/1982 | Murphy et al. | 568/473 |

FOREIGN PATENT DOCUMENTS 1120242 8/1965 United Kingdom ................ 568/473

*Primary Examiner*—Werren B. Lone
*Attorney, Agent, or Firm*—Ralph M. Pritchett

[57] ABSTRACT

In a process for oxidizing methanol to formaldehyde which comprises passing the methanol with molecular oxygen through two sequential silver-based catalysts, with the second of said catalysts being a bed of particulate silver such as, specifically, silver crystals, the process efficiency, and especially the efficiency of the reaction taking place in the second catalyst bed, is improved by controlling (a) the ratio of formaldehyde to methanol in the reactant gases entering the second catalyst bed and (b) the specific reaction rate in said second bed. The specific reaction rate is defined as the quantity of methanol converted in said second bed per unit time per unit of cross-sectional area of the bed.

5 Claims, No Drawings

PROCESS FOR CONVERTING METHANOL TO FORMALDEHYDE

BACKGROUND OF THE INVENTION

This invention relates broadly to the catalytic oxidation of methanol with molecular oxygen to produce formaldehyde. More particularly it relates to those processes in which the catalytic oxidation of methanol is carried out by passing gases comprising methanol and molecular oxygen through two sequential catalyst beds, both of which comprise silver. In particular it relates to such a process in which the second catalyst bed contains particulate silver, especially silver crystals. In a particular embodiment, both catalyst beds consist essentially of silver crystals.

There is an extensive body of prior art dealing with the catalytic oxidation of methanol to form formaldehyde. Some processes, to which the present invention is not directed and which will therefore not be discussed further herein, employ catalysts comprising the oxides of any of a large number of catalytic elements, normally mixtures of the oxides of several elements. Typically such processes are conducted with an excess of oxygen and are characterized by very high conversions even in a single reaction stage. Others, to which the present process improvement is more closely related, employ two sequential reaction stages with the total amount of molecular oxygen being less than that required stoichiometrically to convert the methanol to formaldehyde, hydrogen, and water. Various catalysts are known for processes of this type, including silver, used either on an inert support or else as the metal itself in the form of gauze or crystals. Metallic foam is also a catalyst. Broadly speaking, it is known in these prior-art two-stage processes that such parameters as space velocity in the catalyst beds are significant in controlling the system to optimize process throughput and reaction efficiency. It is also known to introduce additional methanol, molecular oxygen, or both in between the two reaction stages although references to using supplemental methanol between stages where both stages use silver have not been seen. As will be seen hereinbelow, the present invention is directed to controlling two particular reaction parameters in a manner which has not been recognized in the prior art as being significant.

U.S. Pat. No. 3,959,383 (to Northeimer) discloses a two-stage reaction system in which methanol is reacted with molecular oxygen to produce formaldehyde. The first stage is carried out in the presence of a silver gauze catalyst although other forms of silver are not excluded, while the second stage is 20–30 mesh electrolytically-prepared silver crystals. Supplemental air is introduced between the two reaction stages, but supplemental methanol is not. The crux of the invention as disclosed and claimed is the maintenance of certain specified space velocities in the two reaction stages. The ratio of oxygen to methanol is taught as being significant, but there is no teaching that maintaining any particular ratio of formaldehyde to methanol in the feed to the second reaction stage is in any way significant. The incorporation of steam into the reaction mixture prior to the catalytic oxidation is mentioned. Over-all, the teaching of the Northeimer patent is directed primarily to the control of reaction space velocity and oxygen:methanol ratio. The concept of "specific reaction rate" as dealt with in the present invention does not appear in Northeimer.

The use of silver crystals as a methanol-oxidation catalyst is discussed in U.S. Pat. No. 1,968,552 (to Bond) and also in U.S. Pat. No. 1,937,381 (also to Bond). The manufacture of electrolytic silver crystals suitable for use as catalyst in those processes has been generally known in the art at least since the end of World War II, such crystals having been used in Germany during and since the war.

U.S. Pat. No. 2,462,413 (to Meath) discloses a two-stage reaction using a supported silver catalyst in each stage. Inter-stage cooling is employed, and additional reaction air is added between the two stages. U.S. Pat. No. 2,519,788 (to Payne) discloses a two-stage reaction in which the first-stage catalyst is metallic silver while that in the second stage is of the metal oxide type. The first-stage catalyst actually discussed is silver gauze, although the teaching of the patent is not limited to this. The thrust of Payne is that a more complete over-all reaction is obtained if the metallic silver first stage is followed by use of the oxide catalyst (which employs more oxygen but which also brings about a more nearly complete conversion than does silver.)

U.S. Pat. No. 2,908,715 (to Eguchi et al.) discloses a single-stage oxidation over silver catalyst, with space velocity being discussed as a factor which can be manipulated to cope with the problem of localized overheating of the catalyst.

U.S. Pat. No. 2,504,402 (to Field) discloses a multi-stage catalytic oxidation of methanol. Reactants are cooled between stages, and, according to the patentee, any "well-known catalyst" can be employed although oxide catalysts are exemplified. Field specifically discloses the introduction of methanol between the reaction stages, (as distinguished from Northeimer, who adds air but not methanol), but Field also points out that oxygen can be introduced between the stages if desired. He also discloses the use of a "clean-up" catalyst in the last stage to oxidize all of the methanol down to a fraction of a percent. U.S. Pat. Nos. 3,415,866; 3,640,900; and 3,987,107 all disclose adding methanol between a silver first stage catalyst and an oxide-type second stage to increase reaction productivity.

U.S. Pat. No. 3,174,911 (to Webb) discloses a single-stage oxidation using silver catalyst. Finally, Hedley et al. in "The Industrial Chemist," July, 1952, pages 311 to 316, describe formaldehyde production on the industrial scale by using single-stage oxidation over silver crystals. Hedley et al. refer also to the World War II German technology. To summarize the foregoing, the prior art teaches (a) that silver is an effective catalyst for methanol oxidation and that it can be used in any form having an extended surface with electrolytically-prepared crystals being, however, unusually effective, (b) that silver crystals are particularly useful in the second stage of a two-stage process because they are unusually active catalysts, (c) that in multi-stage catalytic oxidations of methanol to formaldehyde it is possible to introduce supplemental methanol, air, or both between the stages along with, if desired, steam, and that (d) the reaction space velocity and the ratio of oxygen (or air) to methanol in the reactants are significant process control parameters.

Obviously also, of course, the prior art discusses extensively such factors as reaction temperature and, of particular importance, the desirability of reducing the temperature rapidly in the reaction product gases exiting from the catalyst bed. In this matter of rapid temperature reduction, incidentally, co-pending U.S. application Ser. No. 286,235 (by Murphy et al.) discloses an unexpectedly effective technique for enhancing the speed of the temperature reduction following the catalytic reaction by employing a tubular aftercooler the tubes of which are packed with inert inserts such as ceramic balls. This particular technique is a useful adjunct to the present invention which will be described hereinbelow.

It is an object of the present invention to identify certain process parameters the proper manipulation of which results in improvements in the chemical efficiency and conversion obtaining when methanol is catalytically oxidized to formaldehyde in a catalytic oxidation reaction system containing two sequential silver-based catalysts. It is another object to improve reaction performance in a two-stage methanol-oxidation reaction system in which the catalyst in the second stage consists essentially of silver crystals. It is another object to provide a method for improving the performance of the reaction system when each reaction stage employs as catalyst a bed of silver crystals. It is a broad object to provide a control scheme employing as interacting control parameters the formaldehyde:methanol ratio in the second-stage feed mixture and the specific reaction rate in the second stage of the reaction.

Other objects will be apparent from the following detailed specification and claims.

BRIEF DESCRIPTION OF THE INVENTION

In accordance with the present invention, the performance of a two-stage methanol-oxidation system employing a silver catalyst in each stage, with the second stage in particular consisting essentially of silver crystals, is improved over the prior art, and/or can be controlled in a manner not suggested in the prior art, by so controlling the composition of the reaction gases entering the second stage catalyst as to maintain in the reaction feed gases (which comprise the vapors of methanol and water along with molecular oxygen and, of course, some formaldehyde which will have been formed in the first reaction stage) a molar ratio of formaldehyde to methanol within the range of about 0.9:1 to about 2.7:1 while also controlling the specific reaction rate of methanol in the second-stage catalyst bed within the range of about 10 to 60 grams of methanol converted per hour per square centimeter of cross-section of said second catalyst bed. The formaldehyde:methanol ratio can be controlled by controlling the methanol conversion in the first catalyst bed (e.g., decreasing the conversion in the first bed will increase the proportion of methanol in the first-stage reaction product) or by, if desired, injecting methanol vapors from an external source into the reactants entering the second catalyst bed. The "specific reaction rate" in the second catalyst bed can be controlled by, for example, the sizing of the bed. That is, providing a bed of increased cross-section will, at a given reactant throughput and conversion rate, reduce the specific reaction rate in that bed. Reducing the catalyst bed cross-section has the effect, of course, of increasing the specific reaction rate. Space velocity can be varied without changing the specific reaction rate. For example, doubling the depth of the bed will halve the space velocity without changing the specific reaction rate if the diameter of the bed is not changed. It will be understood that the present invention is not intended to refute prior-art teachings regarding such parameters as reaction space velocity, air:methanol ratio, etc. as being significant in process control. Rather, the present invention lies in the discovery that, in a multi-stage reaction system, the interstage formaldehyde:methanol ratio and the second-stage specific reaction rate also constitute parameters not previously recognized as being significant but which are in fact significant in obtaining optimum reactor performance such that optimum reaction results are not necessarily restricted to the control limits taught in the prior art.

DETAILED DESCRIPTION OF THE INVENTION

As previously explained, a fundamental difference between the present process and the two-stage silver-catalyzed process of the prior art lies in the combination of (a) the control of the formaldehyde:methanol ratio in the reactant gases entering the second-stage catalyst with (b) the control of the second reaction stage whereby the specific reaction rate of methanol therein is maintained within certain specified limits. Specific details will be explained hereinbelow.

As for the nature of the catalyst used in the two reaction stages, the first-stage catalyst can be any type of silver catalyst as already used in the prior art, although crystals are especially useful. Crystals are not essential to the present invention, however. For example, the first-stage catalyst can be silver gauze, or silver on any suitable inert support as already known in the art, or mossy metallic silver, with or without additives such as small amounts of lead, or foamed metallic silver. Particulate silver is broadly applicable, including not only silver crystals which are, as already noted, especially useful, but also such particulate forms as chopped wire.

The nature of the silver catalyst in the first stage is relatively unimportant. Regardless of the exact nature of the first-stage catalyst, one can, by controlling reactant proportions, effect the desired control of the gas composition between the two reaction stages as desired. For example, to increase the formaldehyde:methanol ratio in the gases leaving the first reaction stage, the conversion in the first stage can be increased. Conversely, to increase the proportion of methanol leaving the first reaction stage, one can decrease the first stage conversion so as to increase the degree of what has been termed "leakage" of methanol unreacted through the first catalyst bed. Generally speaking, the first reaction stage will be so controlled that the ratio of formaldehyde to unreacted methanol in the gases leaving the first stage will be about 4:1 or less. Otherwise, e.g. when the formaldehyde:methanol ratio is much higher than this, one will be, in effect, operating a high-conversion single-stage process typical of the single-stage processes of the prior art, and the full benefits of employing a two-stage system will not be realized.

The heart of the present invention lies in control of the second reaction stage. As previously explained, it is desired that the gases entering the second stage contain formaldehyde and methanol in a molar ratio of about 1.5:1 to about 2.7:1, preferably about 1.7:1 to 2.5:1. This ratio within the second-stage reactant feed gases can be obtained by adjusting the conversion in the first stage as previously explained (that is, raising the conversion will increase the formaldehyde:methanol ratio in the reaction product while lowering this first-stage conversion will lower the ratio of formaldehyde to methanol in the first-stage product). Conversion can be increased by increasing the air:methanol ratio. It is also possible, alternatively or in combination with a decrease in first-stage conversion, to decrease the ratio of formaldehyde to methanol entering the second stage catalyst by introducing supplemental methanol vapor between the two reaction stages. Additional methanol will be accompanied, of course by such quantity of air (or other source of molecular oxygen) as is required in order to provide for the second reaction stage an adequate quantity of molecular oxygen for reaction with the total amount of methanol which will be present in the gases at this stage of the process. About 0.3 to 1.2 mol of $O_2$ per mol of methanol is recommended, preferably about 0.4:1 to 1.0:1.

The specific reaction rate to be maintained in the second catalyst stage is, as previously explained, about 10 to 60 grams of methanol converted per hour per square centimeter of cross-section of the second-stage catalyst bed, the catalyst bed being, as previously explained, normally a finely-divided particulate form of silver, especially silver crystals. Silver crystals ranging in size from about 8 to 80 mesh (U.S. Standard) are preferred, with crystals within the size range of about 8 to 30 mesh being especially preferred. It is sometimes useful to have a gradation in crystal size, e.g. to employ catalyst beds having a lower layer of about 8 to b 16 mesh crystals and an upper layer of about 16 to 30 or 20 to 30 mesh crystals. To clarify any possible misunderstanding as to what is meant by the "cross-section" of the catalyst bed, this is the area of a plane passed through the catalyst bed in a direction normal to the flow of the reacting gases passing through the bed. Ordinarily the catalyst bed will be in the form of a very shallow cylinder, and the cross-section of the bed would, therefore, be the area of one of the faces, e.g., the face exposed to the entering gases, of the cylinder.

The specific reaction rate can be controlled within the presently-specified limits by controlling the rate of introduction of the reactant gases into the second-stage catalyst bed or, alternatively, by adjusting the size of the bed with the rate of introduction of the reactants thereinto being constant. For example, if the specific reaction rate is lower than desired, the cross-section of the second-stage catalyst bed can be reduced. Alternatively, if the specific reaction rate is higher than desired, the cross-section of the second-stage catalyst can be increased or, alternatively, the throughput of the reactant gases can be reduced. Typically, in an actual operating process, with the throughput of the first reaction stage being substantially constant, it is convenient to control the system by introducing supplemental methanol vapor into the second-stage feed gases, the rate of introduction of this supplemental methanol being such as to maintain the desired formaldehyde:methanol ratio and the desired specific reaction rate. It will be understood, of course, that the activity of the catalysts employed in the two reaction stages will set base-line conditions affecting, for example, the broad ranges of space velocity within which each stage will operate and, therefore, the size of the two catalyst beds, or at least the initial size which will be first installed subject to subsequent modification, as for example by adding more or less catalyst to each of the two beds for normal baseline operating conditions.

Typically, when the first-stage catalyst consists essentially of silver crystals of the same type recommended for the second stage, the first stage catalyst bed will be sized for a space velocity of about 50,000 to 200,000 reciprocal hours. More typically, the space velocity in the first stage will be about 90,000 to 180,000 reciprocal hours (based on a temperature of 0° C. and a pressure of one atmosphere for the entering gaseous reactants and based on the total volume of the catalyst bed). In the second reaction stage the space velocity, on the same basis as just specified, will be about 130,000 to 270,000 reciprocal hours. It is to be understood, of course, that these space velocities in the two reaction stages are useful in the preliminary sizing of the catalyst beds, but that employment of the present process improvement will involve such finer adjustment as is necessary to attain the specified formaldehyde:methanol ratio and the specified second-stage specific reaction rate.

The physical design of the catalyst beds is the same as in the prior art. That is, the catalyst is disposed on a suitable horizontal supporting screen positioned as close as is feasible to the tube sheet of an aftercooler heat exchanger, the aftercooler being, preferably, packed with suitably inert inserts for enhancing the heat transfer therein. The arrangement described in co-pending patent application Ser. No. 286,235 by Murphy and McMillan is useful and recommended, with the inserts being ceramic balls.

The composition of the reactant gases fed into the first reaction stage is within the ranges already employed in conventional two-stage silver-catalyzed methanol oxidation processes. For example, the gases entering the first catalyst bed will comprise, by volume, about 37 to 43% methanol, about 8 to 11% oxygen, about 35 to 40% nitrogen, and about 9 to 16% water vapor. The composition of the gases fed into the second catalyst bed is controlled, in accordance with the present invention, in a manner not recognized by the prior art as being significant. Specifically, these gases, which may contain supplemental methanol vapor or not depending on how the first stage has been operated, will typically comprise, by volume, about 13 to 18% formaldehyde, about 12 to 23% water vapor, and sufficient methanol, including supplemental methanol if the composition of the gas leaving the first reaction stage requires supplemental methanol addition, that the molar ratio of formaldehyde to methanol is within the range of about 1.5:1 to 2.7:1. There is also provided, in the gases entering the second reaction stage, sufficient molecular oxygen, typically in the form of air, that the molar ratio of molecular oxygen to methanol is within the range of about 0.4:1 to 1.0:1. More preferably, the quantity of methanol supplied to the second stage catalyst bed, whether as supplemental methanol or as methanol "leaked" through the first stage, is such that the molar ratio of formaldehyde to methanol is within the range of about 1.7:1 to 2.5:1.

It will be understood, of course, that such oxygen as is introduced between the two reaction stages will normally be in the form of air, so that nitrogen is introduced with the oxygen. Generally speaking, the gases entering the second reaction stage will contain roughly 39 to 45% nitrogen and 0.9 to 1.5% carbon dioxide along with the methanol, formaldehyde, hydrogen, and water vapor.

In both reaction stages the incorporation of water vapor into the reaction feedstock is in accordance with principles well known in the prior art, wherein the water vapor content is kept at a level sufficient to avoid the danger of explosion but below that at which the ultimately recovered aqueous formaldehyde solution product would be unacceptably dilute.

The reaction temperatures in the two catalyst beds are typically about 550° to 700° C. inside the first catalyst bed and approximately 550° to 700° C. inside the second bed. In accordance with the established prior art, of course, these temperatures are reduced as rapidly as possible by an aftercooler following each of the reaction stages to avoid product degradation. The temperature of the cooled gases leaving the second stage aftercooler is typically in the range of about 120° to 250° C., as is that of the gases leaving the first-stage aftercooler and that of the gaseous mixture entering the second reaction catalyst bed. Entering the first reaction stage, the temperature of the gaseous feed mixture is approximately 90° to 170° C.

The pressure in both reaction stages is substantially atmospheric. However, a small positive pressure is actually used to maintain gas flow through the system, of course, and also to overcome the small above-atmospheric pressure obtaining in the absorption system which follows the second reaction stage. This absorption system—that is, the product recovery system which is used to scrub the product formaldehyde out of the reaction gases for subsequent conversion to a standard formaldehyde aqueous solution for sale or other use—is entirely identical with such systems as already used in the prior art and is outside the scope of the present invention. Typically, the pressures used in these conventional water-absorption product recovery systems are such that the methanol-oxidation reaction system operates at a pressure of about 0.1 to 1.0 atmosphere gauge, and such pressures are applicable in the present improved process.

The following examples are given to illustrate further the practice of the invention and to show the interaction of some of the parameters affecting two-stage methanol oxidation processes. Examples 4, 5, and 6 are within the scope of the present invention. Examples 1, and 3 are outside its scope, while Example 2 is transitional. In all cases the catalyst in both reaction stages was silver crystals of approximately 20 to 30 mesh (U.S. Standard Gauge) particle size, and in every case both the first-stage and second-stage aftercoolers comprised heat exchangers the tubes of which were packed with ceramic balls to enhance heat transfer and cool the gases as rapidly as possible. Both aftercoolers were also coupled as closely as possible to the catalyst beds.

It will be understood that many variations can be made from the invention as exemplified below within the scope of the invention.

EXAMPLE 1

Operation without Methanol Addition between Stages

A gaseous mixture of methanol (974 mol/hr), water (328 mol/hr), and air (1403 mol/hr) was preheated to 160° C. and passed into the first of two similar reactors connected in series. Each reactor contained a fixed bed of 2.25 kg of silver particles of 99.9% purity. The beds were 8 inches in diameter and about 0.8 inch in depth. Reaction occured in the primary reactor heating the catalyst and products to 677° C. The effluent was rapidly cooled to 195° C. in a closely coupled aftercooler. Approximately 792 mol/hr of the methanol (81.3%) was converted; the products (carbon efficiencies in parentheses) were formaldehyde (91.1%), carbon dioxide (7.95%), and methyl formate (0.91%). The space velocity (liters of gas fed at STP per hour per liter of catalyst) was 92,000 hr$^{-1}$. The products contained formaldehyde:methanol in a molar ratio of 3.98.

To the primary effluent was added 896 mol/hr secondary air. The secondary feed was allowed to react in the secondary reactor; the temperature rose to 666° C. The secondary effluent was rapidly cooled to 195° C. in a closely coupled aftercooler. An additional 171.6 mol/hr of methanol was converted to give a total conversion of 98.9% of that fed to the primary reactor. On the basis of the methanol converted in the secondary reactor, the products (carbon efficiencies in parentheses) were: formaldehyde (25.5%), carbon dioxide (75.0%), and methyl formate (−0.54%). The space velocity in the secondary reactor was 140,000 hr$^{-1}$. The yield of formaldehyde through both reactors was 0.786 mol per mol of methanol fed.

The secondary effluent was passed into an absorber where noncondensable gases were separated and vented and an aqueous solution of 51.2 wt% formaldehyde, 0.65 wt % methanol, and 0.019 wt % formic acid was withdrawn from the bottom.

The following Example 2 complements Example 1 and shows that interstage methanol addition increases second stage efficiency without need for a substantial change in space velocity. Data in Example 2 were obtained using the same catalysts as in Example 1. Catalyst age in Example 1 was 720 hours and in Example 2 it was 1120 hours.

EXAMPLE 2

With Methanol Addition between Stages

A gaseous mixture of methanol (944 mol/hr), water (422 mol/hr), and air (1397 mol/hr) was preheated to 166° C. and passed into the first of two similar reactors connected in series. Each reactor contained a fixed bed of 2.25 kg of silver particles of 99.9% purity. The beds were 8 inches in diameter and about 0.8 inch in depth. Reaction occured in the primary reactor heating the catalyst and products to 692° C. The effluent was rapidly cooled to 195° C. in a closely coupled heat exchanger. Approximately 768 mol/hr of the methanol (81.4%) was converted; the products (carbon efficiencies in parentheses) were: formaldehyde (92.5%), carbon dioxide (6.82%), and methyl formate (0.70%). The space velocity was 94,000 hr$^{-1}$. The products contained formaldehyde:methanol in a molar ratio of 4.03.

Methanol from an auxiliary tank was vaporized and added at a rate of 90.6 mol/hr to the primary effluent. This increased the methanol feed rate to about 267 mol/hr and decreased the formaldehyde:methanol molar feed ratio to 2.67. Secondary air (983 mol/hr) was then added. This stream was allowed to react in the secondary reactor; the temperature rose to 630° C. The secondary effluent was rapidly cooled to 195° C. in a closely coupled heat exchanger. An additional 252 mol/hr of methanol was converted to give a total conversion of 98.6% of the sum of that fed to the primary and secondary reactors. On the basis of the methanol converted in the secondary reactor, the products (carbon efficiencies in parentheses) were: formaldehyde (56.4%), carbon dioxide (42.2%), methyl formate (0.27%), and carbon monoxide (1.02%). The space velocity in the secondary reactor was 149,000 hr$^{-1}$. The yield of formaldehyde through both reactors was 0.824 mol per mol of total methanol fed.

The secondary effluent was passed into an absorber where non-condensable gases were separated and vented and an aqueous solution of 51.2 wt% formaldehyde, 0.93 wt % methanol, and 0.021 wt % formic acid was withdrawn from the bottom.

The following Example 3 demonstrates, in comparison with Example 1, that a change in specific reaction rate was associated with a significant improvement in operating results even though the formaldehyde:methanol ratio was not changed significantly.

EXAMPLE 3

Operation without Methanol Addition between Stages

A gaseous mixture of methanol (1928 mol/hr), water (643 mol/hr), and air (2622 mol/hr) was preheated to 108° C. and passed into the first of two similar reactors connected in series. Each reactor contained a fixed bed of 2.25 kg of silver particles of 99.9% purity. The beds were 8 inches in diameter and about 0.8 inch in depth. Reaction occured in the primary reactor heating the catalyst and products to 648° C. The effluent was rapidly cooled to 195° C. in a closely coupled aftercooler. Approximately 1554 mol/hr of the methanol (80.6%) was converted; the products (carbon efficiencies in parentheses) were formaldehyde (91.0%), carbon dioxide (7.43%), methyl formate (0.97%), and carbon monoxide (0.59%). The space velocity was 176,700 hr$-1$. The products contained formaldehyde:methanol in a molar ratio of 3.79.

To the primary effluent was added 1716 mol/hr secondary air. The secondary feed was allowed to react in the secondary reactor; the temperature rose to 612° C. The secondary effluent was rapidly cooled to 195° C. in a closely coupled aftercooler. An additional 352 mol/hr methanol was converted to give a total conversion of 98.9% of that fed to the primary reactor. On the basis of the methanol converted in the secondary reactor, the products (carbon efficiencies in parentheses) were: formaldehyde (38.1%), carbon dioxide (64.6%), methyl formate (−1.76%), and carbon monoxide (−0.88%). The space velocity in the secondary reactor was 271,400 hr$-1$. The yield of formaldehyde through both reactors was 0.803 mol per mol of methanol fed.

The secondary effluent was passed into an absorber where noncondensable gases were separated and vented and an aqueous solution of 51.4 wt % formaldehyde, 0.63 wt % methanol, and 0.014 wt % formic acid was withdrawn from the bottom.

The following Example 4 complements Example 3 and shows that decreasing the formaldehyde:methanol ratio in the second-stage feed gases increases second stage efficiency even though the space velocity is lower and the rate of methanol reaction is about the same. In this case (Example 4) the ratio was adjusted by adding methanol from an outside source into the second-stage feed mixture. The data in Example 3 were obtained after the catalysts were in use for 336 hours. The data in Example 4 were obtained with different batches of the same catalyst after they had been in use for 144 hours.

EXAMPLE 4

Operation with Methanol Addition between Stages

A gaseous mixture of methanol (1073 mol/hr), water (505 mol/hr), and air (1480 mol/hr) was preheated to 157° C. and passed into the first of two similar reactors connected in series. Each reactor contained a fixed bed of 2.25 kg of silver particles of 99.9% purity. The beds were 8 inches in diameter and about 0.8 inch in depth. Reaction occured in the primary reactor heating the catalyst and products to 627° C. The effluent was rapidly cooled to 195° C. in a closely coupled heat exchanger. Approximately 862 mol/hr of the methanol (80.3%) was converted; the products (carbon efficiencies in parentheses) were: formaldehyde (92.0%), carbon dioxide (7.01%), and methyl formate (0.97%). The space velocity was 104,000 hr$-1$. The products contained formaldehyde:methanol in a molar ratio of 3.75.

Methanol from an auxiliary tank was vaporized and added at a rate of 145.9 mol/hr to the primary effluent. This increased the methanol feed rate to 357 mol/hr and decreased the formaldehyde:methanol molar ratio to 2.22. Secondary air (1133 mol/hr) was then added. This stream was allowed to react in the secondary reactor; the temperature rose to 618° C. The secondary effluent was rapidly cooled to 195° C. in a closely coupled heat exchanger. An additional 340 mol/hr of methanol was converted to give a total conversion of 98.6% of the sum of that fed to the primary and secondary reactors. On the basis of the methanol converted in the secondary reactor, the products (carbon efficiencies in parentheses) were: formaldehyde (69.5%), carbon dioxide (29.6%), and methyl formate (0.86%). The space velocity in the secondary reactor was 168,000 hr$-1$. The yield of formaldehyde through both reactors was 0.844 mol per mol of total methanol fed.

The secondary effluent was passed into an absorber where noncondensable gases were separated and vented and an aqueous solution of 52.5 wt % formaldehyde, 0.86 wt % methanol, and 0.022 wt % formic acid was withdrawn from the bottom.

The following Example 5 complements Example 4 and shows that increasing the "leakage" of unconverted methanol from the primary reactor to decrease the ratio of formaldehyde:methanol in the feed to the secondary reactor is equivalent to interstage methanol addition. The data in Example 5 were obtained with the same catalysts that were used in Example 4, after they had been in use 124 hours.

EXAMPLE 5

Increased Methanol "Leakage" from First Stage to Adjust Second-Stage Feedstock Composition A gaseous mixture of methanol (1360 mol/hr), water (427 mol/hr), and air (1605 mol/hr) was preheated to 146° C. and passed into the first of two similar reactors connected in series. Each reactor contained a fixed bed of 2.25 kg of silver particles of 99.9% purity. The beds were 8 inches in diameter and about 0.8 inch in depth. Reaction occured in the primary reactor heating the catalyst and products to 591° C. The effluent was rapidly cooled to 195° C. in a closely coupled aftercooler. Approximately 968 mol/hr of the methanol (71.1%) was converted; the products (carbon efficiencies in parentheses) were: formaldehyde (92.0%), carbon dioxide (6.21%), and methyl formate (1.75%). The space velocity was 115,400 hr$-1$. The products contained formaldehyde:methanol in a molar ratio of 2.27.

To the primary effluent was added 1238 mol/hr of secondary air. The secondary feed was allowed to react in the secondary reactor; the temperature rose to 646° C. The secondary effluent was rapidly cooled to 195° C. in a closely coupled aftercooler. An additional 375 mol/hr methanol was converted to give a total conversion of 98.7% of that fed to the primary reactor. On the basis of the methanol converted in the secondary reactor, the products (carbon efficiencies in parentheses)

were: formaldehyde (68.6%), carbon dioxide (31.0%), and methyl formate (0.34%). The space velocity in the secondary reactor was 182,100 hr$^{-1}$. The yield of formaldehyde through both reactors was 0.844 mol per mol of methanol fed.

The secondary effluent was passed into an absorber where non-condensable gases were separated and vented and an aqueous solution of 52.9 wt % formaldehyde, 0.82 wt % methanol, and 0.019 wt % formic acid was withdrawn from the bottom.

The following Example 6 illustrates what is considered to be, in view of the foregoing, a preferred embodiment of the invention.

EXAMPLE 6

A gaseous mixture consisting essentially of methanol, water vapor, and air, in a mol ratio of 1.00:0.36:1.19, was preheated to 105° C. and passed into the first of two similar reactors connected in series. Each reactor contained a fixed bed of silver crystals of 99.9% purity and of a particle size ranging from about 8 to 30 mesh (U.S. Standard Gauge). The first-stage bed was about 0.7 inch deep and the second stage about 0.8 inch deep. Both beds comprised a lower layer of 8–16 mesh crystals and an upper layer (greater than half of the total bed in each case) that was of 20–30 mesh size in both the first bed and the second bed.

Approximately 10.5 gram mols of the mixed reactant gases were passed through the first bed per hour per square centimeter of bed cross-section. Reaction occurred in the primary (first stage) reactor, heating the catalyst and reaction products to 566° C. The effluent gases from the first bed were rapidly cooled to 200° C. in a closely-coupled aftercooler. Approximately 68.5% of the methanol in the feed gases was converted; the products (carbon efficiencies in parentheses) were: formaldehyde (90.0%), carbon dioxide (6.95%), carbon monoxide (0.10%), and methyl formate (2.90%). The space velocity was approximately 133,000 hr$^{-1}$. The products contained formaldehyde and methanol in a molar ratio of 1.91, this ratio being satisfactory for second-stage reaction feed stock so that there was no need to add supplemental methanol between the stages.

To the first-stage reaction product there was then added secondary air, in an amount of approximately 2.68 mol per mol of the unreacted methanol which was still present. The resulting secondary feed mixture was then allowed to react in the secondary reactor; the temperature rose to 630° C. The secondary reactor effluent was then rapidly cooled to 200° C. in a closely-coupled aftercooler. Methanol additionally converted in the second stage amounted to 0.301 mol per mol of methanol initially introduced into the first stage, giving a total conversion across the two stages of 98.6% of the methanol initially fed to the primary reactor. On the basis of the methanol converted in the secondary reactor the products (carbon efficiencies in parentheses) were: formaldehyde (64.6%), carbon dioxide (35.7%), carbon monoxide (1.23%), and methyl formate (−1.5%). The yield of formaldehyde through both reactors was 0.812 mol per mol of methanol initially fed into the first stage. The space velocity in the secondary reactor was 193,000 hr$^{-1}$. The specific reaction rate in the second-stage catalyst bed was 39.7 grams of methanol converted per hour per square centimeter of bed cross-section.

The following tabulation summarizes the data set forth in the preceding examples. Also presented for comparison are comparable information calculated from U.S. Pat. Nos. 3,959,383 and 4,076,754, which are taken as typical of the prior art. It is to be understood that precise comparisons between the presently-obtained results and those set forth in the two U.S. patents are not intended. Rather, it is intended to point out that the present improved process relies on different control parameters than previously employed with good operating results nevertheless being obtained.

TABLE 1

| Data Source | *Specific Reaction Rate Stage 1 | *Specific Reaction Rate Stage 2 | HCHO/CH$_3$OH Molar Ratio | Stage 2 Eff'y. % |
|---|---|---|---|---|
| U.S. 3,959,383: Ex. 1 | 153.8 | 61.3 | 2.13 | |
| U.S. 3,959,383: Ex. 2 | 176.6 | 79.5 | 1.94 | 65.7 |
| U.S. 3,959,383: Ex. 3 | 177.1 | 76.4 | 2.13 | 62.6 |
| U.S. 4,076,754: | 400 | 120 | ca 2.8 | |
| Present Process Ex. 1 | 78.2 | 17.0 | 3.98 | 25.5 |
| Present Process Ex. 2 | 75.9 | 24.9 | 2.67 | 56.4 |
| Present Process Ex. 3 | 153.5 | 34.8 | 3.79 | 38.1 |
| Present Process Ex. 4 | 85.2 | 33.6 | 2.22 | 69.5 |
| Present Process Ex. 5 | 95.6 | 37.0 | 2.27 | 68.6 |
| Present Process Ex. 6 | 90.4 | 39.7 | 1.91 | 64.6 |

*Grams methanol converted per hour per sq cm of catalyst bed cross-sectional area.

The embodiments of the invention in which an exclusive claim or privilege is claimed are:

1. In a process for converting methanol to formaldehyde by (a) passing a gaseous first-stage feedstock mixture comprising methanol, water, and molecular oxygen at an elevated temperature of about 90° to 170° C. and substantially atmospheric pressure through a first bed of silver catalyst operating at about 550° to 700° C. to form a gasesous first-stage reaction product comprising formaldehyde and methanol; (b) cooling said first-stage reaction product to about 120° to 250° C.; and (c) passing a gaseous second-stage feedstock mixture comprising said cooled first-stage reaction product at an elevated temperature of about 120° to 250° C. through a second bed of silver catalyst operating at about 550° to 700° C., which bed comprises particulate silver, to form a gaseous second-stage reaction product, the improvement which comprises:

adjusting the composition of said gasesous second-stage feedstock mixture so as to maintain the molar ratio of formaldehyde to methanol therein within the range of about 0.9:1 to about 2.7:1 while also controlling the specific reaction rate of methanol in said second bed of silver catalyst within the range of about 10 to 60 grams of methanol converted per hour per square centimeter of cross-section of said second bed of silver catalyst.

2. The improvement of claim 1 wherein both of said catalyst beds are particulate silver and said second catalyst bed is silver crystals ranging in size from about 8 to 30 mesh.

3. The improvement of claim 1 wherein said molecular oxygen is supplied to said conversion process as air.

4. The improvement of claim 3 wherein the gases fed to said first catalyst bed comprise, by volume, about 37 to 43% methanol, about 8 to 11% oxygen, about 35 to 40% nitrogen, and about 9 to 16% water and wherein the gases fed to said second catalyst bed comprise, by volume, about 13 to 18% formaldehyde, about 12 to 23% water, sufficient methanol that the molar ratio of formaldehyde to methanol is within the range of about 0.9:1 to 2.7:1 and sufficient molecular oxygen that the molar ratio of molecular oxygen to methanol is within the range of about 0.4:1 to 1.0:1.

5. The improvement of claim 4 wherein the quantity of methanol supplied to said second catalyst bed is such that the molar ratio of formaldehyde to methanol is within the range of about 1.7:1 to 2.5:1 and wherein the specific reaction rate in said second catalyst bed is within the range of about 10 to 60 grams of methanol converted per hour per square centimeter of cross-section of said catalyst bed.

* * * * *